(12) United States Patent
Tseng et al.

(10) Patent No.: US 10,143,383 B2
(45) Date of Patent: Dec. 4, 2018

(54) ATTACHABLE MONITORING DEVICE

(71) Applicants: Chun-Hao Tseng, Taipei (TW); Shih-Chien Lin, Taipei (TW); Ho-Yi Chang, Taipei (TW); Kai-Chieh Chang, Taipei (TW)

(72) Inventors: Chun-Hao Tseng, Taipei (TW); Shih-Chien Lin, Taipei (TW); Ho-Yi Chang, Taipei (TW); Kai-Chieh Chang, Taipei (TW)

(73) Assignee: iWEECARE Co., Ltd., Taipei (TW)

( * ) Notice: Subject to any disclaimer, the term of this patent is extended or adjusted under 35 U.S.C. 154(b) by 549 days.

(21) Appl. No.: 14/793,737

(22) Filed: Jul. 7, 2015

(65) Prior Publication Data
US 2016/0007861 A1    Jan. 14, 2016

Related U.S. Application Data

(60) Provisional application No. 62/022,188, filed on Jul. 8, 2014.

(51) Int. Cl.
*A61B 5/01* (2006.01)
*A61B 5/00* (2006.01)
*G06F 19/00* (2018.01)
*G16H 40/67* (2018.01)
(Continued)

(52) U.S. Cl.
CPC .............. *A61B 5/01* (2013.01); *A61B 5/0022* (2013.01); *A61B 5/6801* (2013.01); *A61B 5/6833* (2013.01); *G06F 19/00* (2013.01); *G16H 40/67* (2018.01); *A61B 5/024* (2013.01); *A61B 5/0816* (2013.01); *A61B 5/441* (2013.01);
(Continued)

(58) Field of Classification Search
CPC ....... A61B 5/01; A61B 5/0022; A61B 5/6801; A61B 5/6833
USPC .......................................................... 600/595
See application file for complete search history.

(56) References Cited

U.S. PATENT DOCUMENTS 3,992,225 A * 11/1976 Sykes ................... H01M 2/105
                                                                361/744
5,677,515 A * 10/1997 Selk ...................... H05K 1/0221
                                                                174/250

(Continued)

OTHER PUBLICATIONS

"Microstrip Antenna," by Wikipedia, The Free Encyclopedia, Aug. 14, 2012, availble at https://web.archive.org/web/20120814232950/https://en.wikipedia.org/wiki/Microstrip_antenna.*

*Primary Examiner* — Daniel Cerioni
(74) *Attorney, Agent, or Firm* — JCIPRNET

(57) ABSTRACT

An attachable monitoring device includes a battery unit, a wiring board unit and a physical condition sensor and an adhesive. The battery unit includes a top surface, a bottom surface and a plurality of side surfaces connecting the top surface and the bottom surface. The wiring board unit covers the top surface, the bottom surface and one of the side surfaces and electrically connected to the battery unit. The wiring board unit includes a printed antenna printed on a first outer surface of the wiring board unit. The physical condition sensor is disposed on a second outer surface of the wiring board unit opposite to the first outer surface. The physical condition sensor includes a sensing region for contacting a user to detecting a physical-condition signal of the user. The adhesive is disposed on the wiring board unit for being attached to the user.

18 Claims, 4 Drawing Sheets

(51) Int. Cl.
*A61B 5/024* (2006.01)
*A61B 5/08* (2006.01)

(52) U.S. Cl.
CPC ........... *A61B 5/6814* (2013.01); *A61B 5/6819* (2013.01); *A61B 5/6823* (2013.01); *A61B 5/6824* (2013.01)

(56) References Cited

U.S. PATENT DOCUMENTS

| | | | | |
|---|---|---|---|---|
| 2010/0328736 | A1* | 12/2010 | Ozawa | H04N 1/1017 358/494 |
| 2011/0050532 | A1* | 3/2011 | Liu | H01Q 9/145 343/846 |
| 2011/0213225 | A1* | 9/2011 | Bernstein | G06Q 50/22 600/309 |
| 2015/0071325 | A1* | 3/2015 | Kuroyama | A61B 5/01 374/134 |
| 2016/0345875 | A1* | 12/2016 | Schimmoeller | A61B 5/6847 |

* cited by examiner

ATTACHABLE MONITORING DEVICE

CROSS-REFERENCE TO RELATED APPLICATION

This application claims the priority benefit of U.S. provisional application Ser. No. 62/022,188, filed on Jul. 8, 2014. The entirety of the above-mentioned patent application is hereby incorporated by reference herein and made a part of this specification.

BACKGROUND OF THE INVENTION

Field of the Invention

The present invention generally relates to a monitoring device. More particularly, the present invention relates to attachable monitoring device for monitoring physical condition of a user.

Description of Related Art

Physical condition monitoring devices are well known and in common use worldwide. In general, such devices usually depend upon some form of body contact in order to measure the temperature of a human subject by contact with the skin of the subject. Monitoring of physical conditions is becoming more necessary as an adjunct to home care and supervision for the elderly, and also for infants, small children, female, pregnant women, athletes, outdoor sportsmen who typically may not be able to actively participate in the monitoring. Various methods have been developed for patient monitoring, usually in conjunction with hospital or other health care personnel. Although such monitoring devices are useful, they are unable to reduce the size thereof since the antenna for wireless communication and the sensor for detecting physical conditions need to be separated for certain distance to avoid interference. Therefore, the monitoring devices direct contacting the human subject suffer from the drawback of causing discomfort to the human subject.

SUMMARY OF THE INVENTION

Accordingly, the present invention is directed to an attachable monitoring device for monitoring physical condition of a user, which is smaller n size to provide better comfort to the user.

The present invention provides an attachable monitoring device for detecting physical condition of a user includes a battery unit, a wiring board unit, a physical condition sensor and an adhesive. The battery unit includes a top surface, a bottom surface opposite to the top surface and a plurality of side surfaces connecting the top surface and the bottom surface. The wiring board unit covers the top surface, the bottom surface and one of the side surfaces and electrically connected to the battery unit. The wiring board unit includes a printed antenna printed on a of the wiring board unit. The physical condition sensor is disposed on a second outer surface of the wiring board unit opposite to the first outer surface. The physical condition sensor includes a sensing region for contacting the user to detecting a physical-condition signal of the user. The adhesive is disposed on the wiring board unit for being attached to a body of the user.

According to an embodiment of the present invention, the wiring board unit further includes a power pad contacting the battery unit for electrically connecting the battery unit and the wiring board unit.

According to an embodiment of the present invention, the wiring board unit is a flexible printed circuit board bended to cover the top surface, the bottom surface and the one of the side surfaces.

According to an embodiment of the present invention, the wiring board unit includes a first printed circuit board, a second printed circuit board and a connector. The first printed circuit board covers the top surface. The second printed circuit board covers the bottom surface. The connector covers the one of the side surfaces and connects the first printed circuit board and the second printed circuit board for electrically connecting the first printed circuit board and the second printed circuit board.

According to an embodiment of the present invention, the printed antenna is disposed on the first printed circuit board, and the physical condition sensor is disposed on the second printed circuit board.

According to an embodiment of the present invention, the first printed circuit board further includes a plurality of first pins. The second printed circuit board further includes a plurality of second pins. Two opposite ends of the connector are engaged with the first pins and the second pins respectively.

According to an embodiment of the present invention, the wiring board unit includes a first printed circuit board and a second printed circuit board. The first printed circuit board covers the top surface and includes a plurality of pin. The second printed circuit board covers the bottom surface and includes a connector corresponding to the pins. The connector covers the one of the side surfaces and engaged with the pins for electrically connecting the first printed circuit board and the second printed circuit board.

According to an embodiment of the present invention, the printed antenna is disposed on the first printed circuit board, and the physical condition sensor is disposed on the second printed circuit board.

According to an embodiment of the present invention, the wiring board unit includes a first printed circuit board, a flexible printed circuit board and a second printed circuit board. The first printed circuit board covers the top surface and is connected to the flexible printed circuit board. The second printed circuit board covers the bottom surface and includes a connector. The flexible printed circuit board is bended to cover the one of the side surfaces and engaged with the connector for electrically connecting the first printed circuit board and the second printed circuit board.

According to an embodiment of the present invention, the printed antenna is disposed on the first printed circuit board, and the physical condition sensor is disposed on the second printed circuit board.

According to an embodiment of the present invention, the wiring board unit includes a flexible printed circuit board and a printed circuit board. The flexible printed circuit board is bended to cover the top surface and the one of the side surfaces. The printed circuit board covers the bottom surface and includes a connector engaged with the flexible printed circuit board for electrically connecting the first printed circuit board and the second printed circuit board.

According to an embodiment of the present invention, the printed antenna is disposed on the flexible printed circuit board, and the physical condition sensor is disposed on the printed circuit board.

According to an embodiment of the present invention, the attachable monitoring device further includes a wireless communication switch disposed on the first outer surface and electrically connected to the printed antenna.

According to an embodiment of the present invention, the attachable monitoring device further includes an isolation enclosure covering the battery unit and the wiring board unit and exposing the sensing region.

According to an embodiment of the present invention, materials of the isolation enclosure includes thermal plastic materials, and the isolation enclosure is formed by injection molding.

According to an embodiment of the present invention, the attachable monitoring device further includes a wireless communication switch electrically connected to the printed antenna, and the isolation enclosure exposing the wireless communication switch.

According to an embodiment of the present invention, the attachable monitoring device further includes an isolation coating filled between the isolation enclosure and the wiring board unit.

According to an embodiment of the present invention, the isolation coating further includes an electrical insulation coating and a waterproof coating.

According to an embodiment of the present invention, the adhesive is disposed on the second outer surface and exposes the sensing region.

According to an embodiment of the present invention, the adhesive is disposed on the first outer surface and a peripheral region of the adhesive is attached to the body of the user.

Based on the description stated above, the attachable monitoring device of the present invention adopts the wiring board unit covering the top surface, the bottom surface and one of the side surfaces of the battery unit and electrically connected to the battery unit 110. With such configuration, the wiring board unit can be electrically connect two opposite surfaces of the battery unit, so that the components of the attachable monitoring device can be disposed on the two opposite surfaces of the battery unit, so as to improve space utilization of the attachable monitoring device and further reduce the overall size of the attachable monitoring device. In addition, the printed antenna and the physical condition sensor of the attachable monitoring device can be disposed at two opposite surface of the wiring board unit respectively, so as to keep a certain distance between the printed antenna and the physical condition sensor to avoid interference. Therefore, the attachable monitoring device of the present invention can also improve the performance thereof without increasing the length of the attachable monitoring device.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
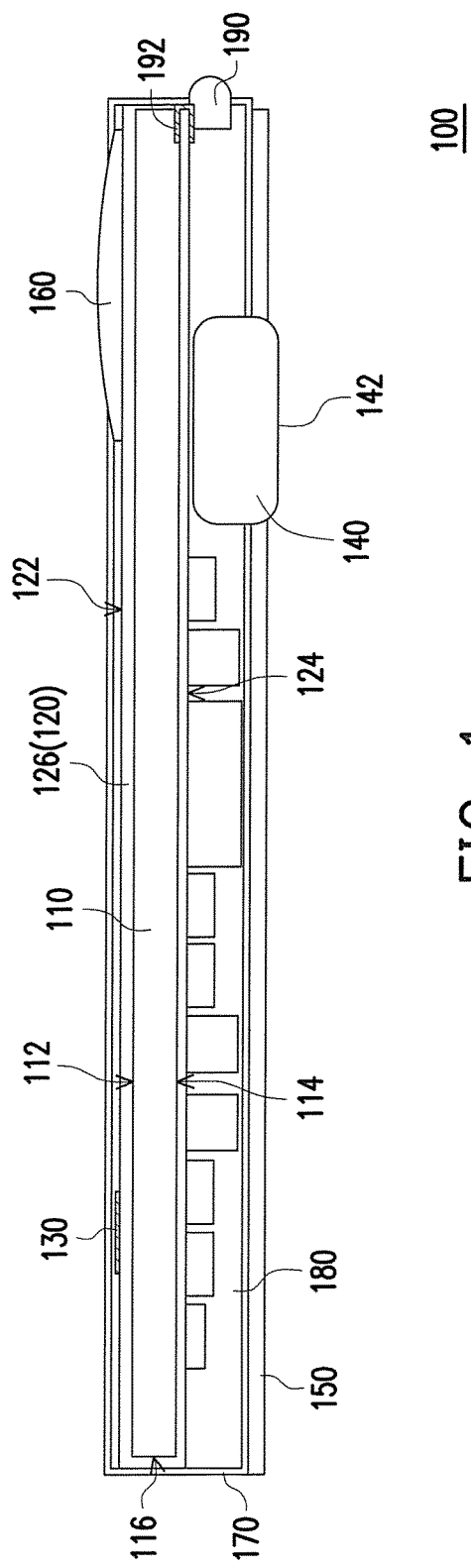
FIG. 1 illustrates a cross-sectional view of an attachable monitoring device according to an embodiment of the invention.

In the following detailed description of the preferred embodiments, reference is made to the accompanying drawings which form a part hereof, and in which are shown by way of illustration specific embodiments in which the invention may be practiced. In this regard, directional terminology, such as "top," "bottom," "front," "back," etc., is used with reference to the orientation of the Figure(s) being described. The components of the invention can be positioned in a number of different orientations. As such, the directional terminology is used for purposes of illustration and is in no way limiting. The use of "including," "comprising," or "having" and variations thereof herein is meant to encompass the items listed thereafter and equivalents thereof as well as additional items. Unless limited otherwise, the terms "connected," "coupled," and "disposed" and variations thereof herein are used broadly and encompass direct and indirect connections, couplings, and mountings. Accordingly, the drawings and descriptions will be regarded as illustrative in nature and not as restrictive. Wherever possible, the same reference numbers are used in the drawings and the description to refer to the same or like parts.

FIG. 1 illustrates a cross-sectional view of an attachable monitoring device according to an embodiment of the invention. Referring to FIG. 1, in the present embodiment, an attachable monitoring device 100 may be attached to a body of a user and configured for detecting physical condition of the user. For example, the attachable monitoring device 100 may be attached to a chest, a wrist, an armpit, a groin, a forehead, a front part of nostrils or a back of the user to detect pulse, heart rate, body temperature, perspiration, respiration, skin humidity, etc., but, of course, the present invention is not limited thereto. The attachable monitoring device 100 includes a battery unit 110, a wiring board unit 120 having a printed antenna printed 130 thereon, a physical condition sensor 140 and an adhesive 150. The adhesive 150 is disposed on the wiring board unit 120 for being attached to the body of the user.

In detail, the battery unit 110 includes a top surface 112, a bottom surface 114 opposite to the top surface 112 and a plurality of side surfaces 116 connecting the top surface 112 and the bottom surface 114. The wiring board unit 120 covers the top surface 112, the bottom surface 114 and one of the side surfaces 116 and electrically connected to the battery unit 110. In the present embodiment, the wiring board unit 120 is a flexible printed circuit board 126, and the flexible printed circuit board 126 is bended to cover the top surface 112, the bottom surface 114 and the one of the side surfaces 116 of the battery unit 110. Therefore, owing to the flexibility thereof, the flexible printed circuit board 126 can be bended to electrically connect two opposite surfaces, i.e. the top surface 112 and the bottom surface 114, of the battery unit 110, so that the components of the attachable monitoring device 100 can be disposed on the two opposite surfaces of the battery unit 110, so as to improve the space utilization of the attachable monitoring device 100 and further reduce the overall size of the attachable monitoring device 100. Also, the flexible printed circuit board 126 provides flexibility to the attachable monitoring device 100, so as to provide better comfort to the user when the attachable monitoring device 100 is in direct contact with the body of the user.

To be specific, the length of the attachable monitoring device 100 may be minimized to about 2.6 cm, and the width of the attachable monitoring device 100 may be minimized to about 2 cm. Regarding the thickness, the wiring board unit 120 and the battery unit 110 jointly form a core portion of the attachable monitoring device 100, and the thickness of the core portion may be minimized to about 0.92 mm. Of course, the numbers listing herein are merely for illustration, and the present invention is not limited thereto.

Figure 2:
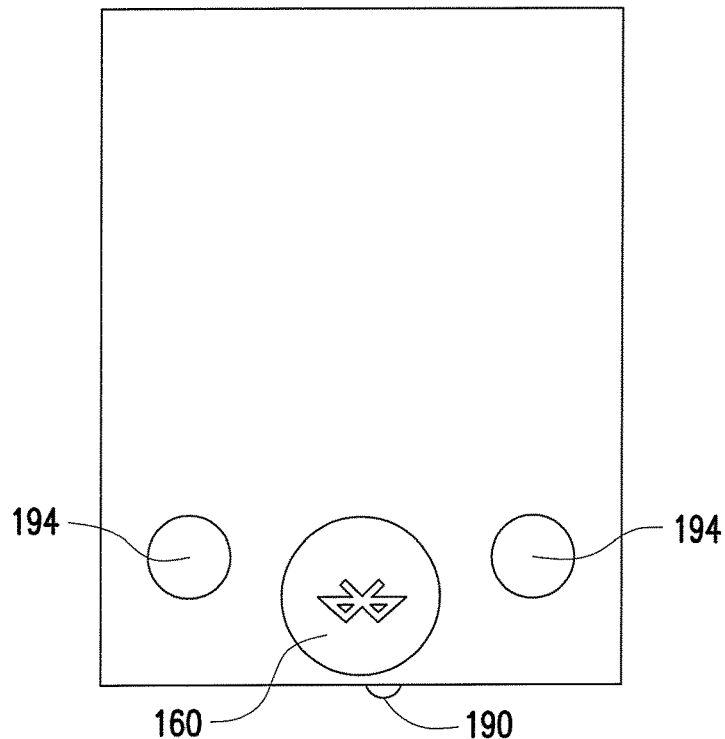
FIG. 2 illustrates a top view of an attachable monitoring device according to an embodiment of the invention.
Figure 3:
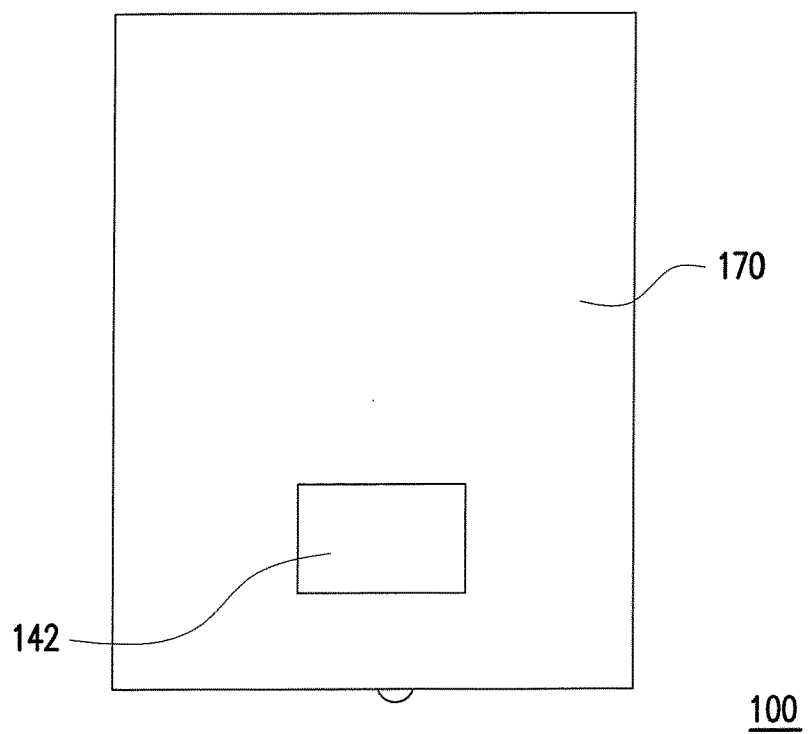
FIG. 3 illustrates a bottom view of an attachable monitoring device according to an embodiment of the invention.

FIG. 2 illustrates a top view of an attachable monitoring device according to an embodiment of the invention. FIG. 3 illustrates a bottom view of an attachable monitoring device according to an embodiment of the invention. Referring to FIG. 1 to FIG. 3, in the present embodiment, the wiring board unit 120 may include a printed antenna 130, a first outer surface 122, and a second outer surface 124 opposite to the first outer surface 122. The printed antenna 130 may be implemented on the first outer surface 122 by, for example, printing process. The physical condition sensor 140 is disposed on the second outer surface 124 of the wiring board unit 120. Namely, the printed antenna 130 and the physical condition sensor 140 are disposed at two opposite surface of the wiring board unit 120 respectively, so as to keep a certain distance between the printed antenna 130 and the physical condition sensor 140 to avoid interference without increasing the length of the attachable monitoring device 100.

The physical condition sensor 140 includes a sensing region 142 for contacting the user to detect a physical-condition signal of the user. The material of the sensing region 142 may be metal such as stainless steel, nickel, copper, gold, silver, etc. Of course, the present invention is lot limited thereto. In the present embodiment, the physical condition sensor 140 may be a thermometer for detecting a body temperature of the user, but, of course, the present embodiment is merely for illustration and does not limit the present invention. The attachable monitoring device 100 further includes a wireless communication switch 160 as shown in FIG. 1 and FIG. 2. The wireless communication switch 160 is disposed on the first outer surface 122 and electrically connected to the printed antenna 130, such that the physical-condition signals detected by the physical condition sensor 140 can be uploaded to the cloud via Bluetooth, Wi-Fi, third generation (3G), Long Term Evolution (LTE), etc., by pressing the wireless communication switch 160 to turn on the wireless communication. In the present embodiment, the attachable monitoring device 100 can associate with both internet (on-line) and telecommunication (off-line) networks to perform real-time early warning and/or physical condition prediction (for fertility) to inform caregivers in time.

In addition, the wiring board unit 120 further includes a power switch 190, a power pad 192 as shown in FIG. 1 and charging pad 194 as shown in FIG. 2. The power pad 192 contacts the battery unit 110 to electrically connect the battery unit 110 and the wiring board unit 120. The power switch 190 is electrically connected to the power pad 192, so the user can turn on and off the attachable monitoring device 100 by pressing the power switch 190. The charging pad 194 may be disposed at the first outer surface 122 and electrically connected to the battery unit 110. The charging pad 194 as shown in FIG. 2 is exposed to be able to connect to a charger, so as to charge the battery unit 110 by a wall charger or a USB port.

Moreover, the attachable monitoring device 100 may further includes an isolation enclosure 170 covering the battery unit 110 and the wiring board unit 120 to prevent water infiltrating into the attachable monitoring device 100. In the present embodiment, the isolation enclosure 170 may also enclose other components, parts, chipsets of the attachable monitoring device 100. The isolation enclosure 170 exposes the sensing region 142, the charging pad 194 and the wireless communication switch 190 as shown in FIG. 2 and FIG. 3. In the present embodiment, the isolation enclosure 170 may be formed by injection molding. Accordingly, the materials of the isolation enclosure 170 may include thermal plastic materials such as polyethylene terephthalate (PET), silicone, thermoplastic urethane (TPU), thermoplastic rubber (TPR), thermoplastic elastomer (TPE), thermoplastic silicone vulcanizate (TPSiV®) or other suitable materials. In addition, the attachable monitoring device 100 may further includes an isolation coating 180 filled between the isolation enclosure 170 and the wiring board unit 120. The isolation coating 180 includes an electrical insulation coating and a waterproof coating.

Figure 4:
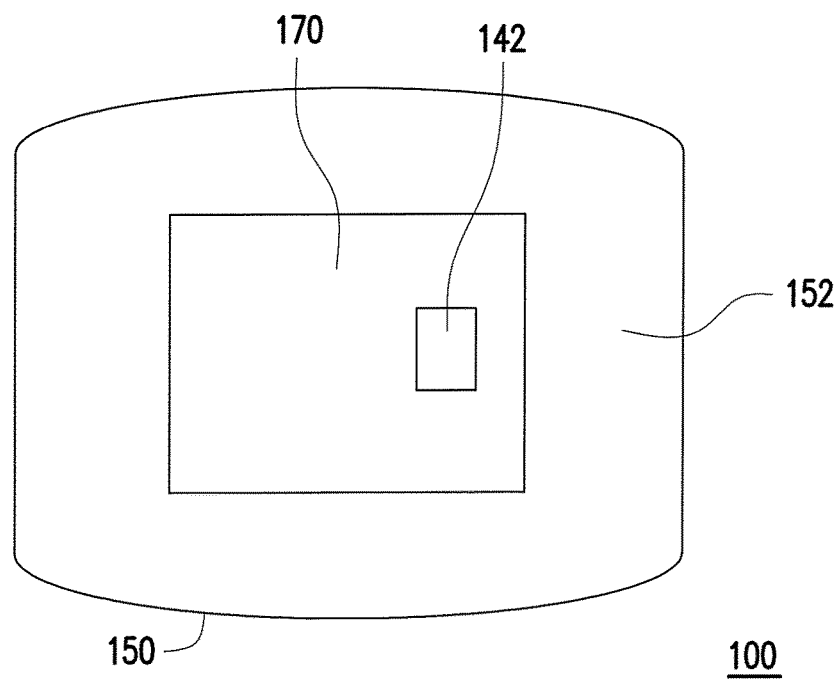
FIG. 4 illustrates a bottom view of an attachable monitoring device according to another embodiment of the invention.

FIG. 4 illustrates a bottom view of an attachable monitoring device according to another embodiment of the invention. Referring to both FIG. 1 and FIG. 4, in the embodiment shown in FIG. 1, the adhesive 150 may be a double-sided tape which is disposed on the second outer surface 124 of the wiring board 120. To be more specific, the adhesive 150 is disposed on the isolation enclosure 170 corresponding to the second outer surface 124, such that the attachable monitoring device 100 can be attached to the body of the user by the adhesive 150. The adhesive 150 exposes the sensing region 142 of the physical condition sensor 140, so the sensing region 142 can contact the body of the user when the attachable monitoring device 100 can be attached to the body of the user. However, in the embodiment shown in FIG. 4, the adhesive 150 may be a one-sided tape disposed on the first outer surface 122. The size of the adhesive 150 is greater than the size of the core portion, so when the adhesive 150 is disposed on the first outer surface 122, a peripheral region 152 of the adhesive 150 would be exposed, so that the attachable monitoring device 100 can be attached to the body of the user by the peripheral region 152 of the adhesive 150 as shown in FIG. 4.

Figure 5:
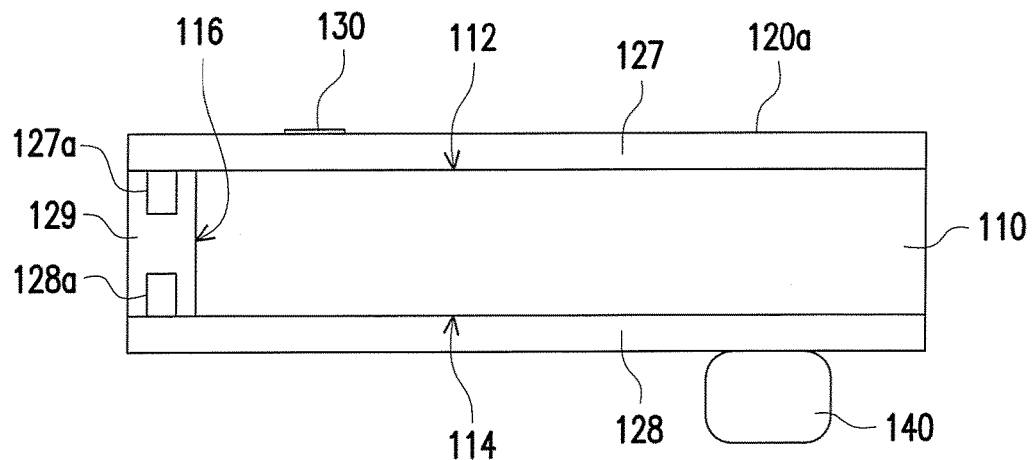
FIG. 5 illustrates a partial cross-sectional view of an attachable monitoring device according to another embodiment of the invention.

FIG. 5 illustrates a partial cross-sectional view of an attachable monitoring device according to another embodiment of the invention. It is noted that the attachable monitoring device 100a shown in FIG. 5 contains many features same as or similar to the attachable monitoring device 100 disclosed earlier with FIG. 1. For purpose of clarity and simplicity, detail description of same or similar features may be omitted; also, the attachable monitoring device 100a shown in FIG. 5 merely illustrate the core portion (the wiring board unit and the battery unit) thereof, and detail illustration of same or similar features are omitted herein.

The main differences between the attachable monitoring device 100a and the attachable monitoring device 100 are that the wiring board unit 120a includes a first printed circuit board 127, a second printed circuit board 128 and a connector 129. The first printed circuit board 127 covers the top surface 112 of the battery unit 110, and the printed antenna 130 is disposed on the first printed circuit board 127. The second printed circuit board 128 covers the bottom surface 114 of the battery unit 110, and the physical condition sensor 140 is disposed on the second printed circuit board 128. The connector 129 covers the one of the side surfaces 116 and connects the first printed circuit board 127 and the second printed circuit board 128 for electrically connecting the first printed circuit board 127 and the second printed circuit board 128. To be more specific, the first printed circuit board 127 further includes a plurality of first pins 127a. The second printed circuit board 128 further includes a plurality of second pins 128a. Two opposite ends of the connector 129 are engaged with the first pins 127a and the second pins 128a respectively, so as to electrically connect the first printed circuit board 127 and the second printed circuit board 128.

Figure 6:
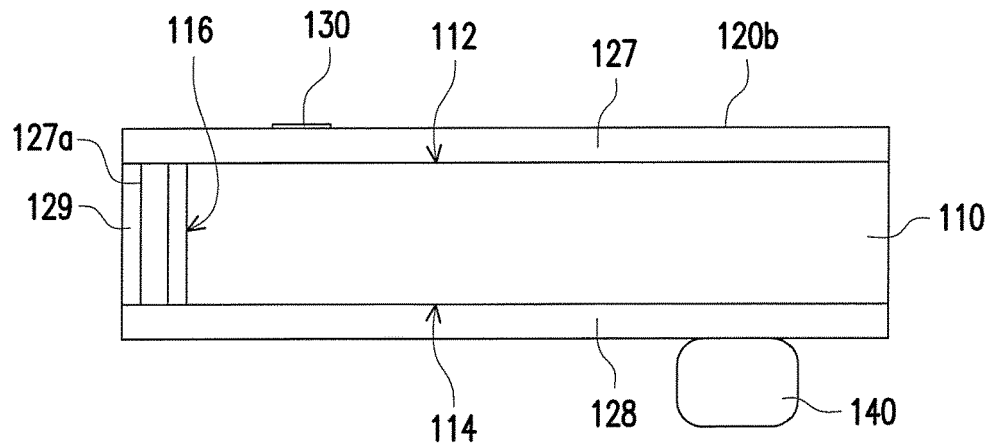
FIG. 6 illustrates a partial cross-sectional view of an attachable monitoring device according to another embodiment of the invention.

FIG. 6 illustrates a partial cross-sectional view of an attachable monitoring device according to another embodiment of the invention. It is noted that the attachable monitoring device 100b shown in FIG. 6 contains many features same as or similar to the attachable monitoring device 100 disclosed earlier with FIG. 1. For purpose of clarity and simplicity, detail description of same or similar features may be omitted; also, the attachable monitoring device 100b shown in FIG. 6 merely illustrate the core portion (the wiring board unit and the battery unit) thereof, and detail illustration of same or similar features are omitted herein.

The main differences between the attachable monitoring device 100a and the attachable monitoring device 100 are that the wiring board unit 120b includes a first printed circuit board 127 and a second printed circuit board 128. The first printed circuit board 127 covers the top surface 112 of the battery unit 110 and includes a plurality of pin 127a. The printed antenna 130 is disposed on the first printed circuit board 127. The second printed circuit board 128 covers the bottom surface 114 of the battery unit 110 and includes a connector 129 corresponding to the pins 127a. The physical condition sensor 140 is disposed on the second printed circuit board 128. The connector 129 covers the one of the side surfaces 116 and engaged with the pins 127a for electrically connecting the first printed circuit board 127 and the second printed circuit board 128.

Figure 7:
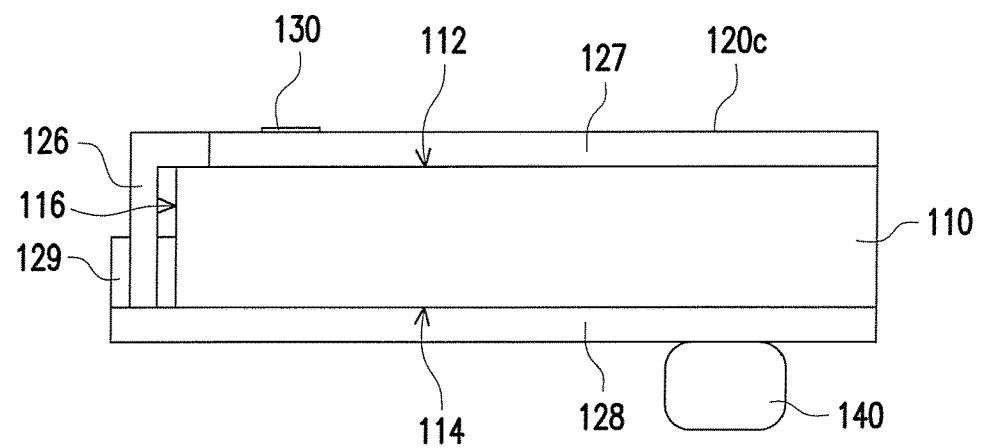
FIG. 7 illustrates a partial cross-sectional view of an attachable monitoring device according to another embodiment of the invention.

FIG. 7 illustrates a partial cross-sectional view of an attachable monitoring device according to another embodiment of the invention. It is noted that the attachable monitoring device 100c shown in FIG. 7 contains many features same as or similar to the attachable monitoring device 100 disclosed earlier with FIG. 1. For purpose of clarity and simplicity, detail description of same or similar features may be omitted; also, the attachable monitoring device 100c shown in FIG. 7 merely illustrate the core portion (the wiring board unit and the battery unit) thereof, and detail illustration of same or similar features are omitted herein.

The main differences between the attachable monitoring device 100c and the attachable monitoring device 100 are that the wiring board unit 120c includes a first printed circuit board 127, a flexible printed circuit board 126 and a second printed circuit board 128. The first printed circuit board 127 covers the top surface 112 of the battery unit 110 and is connected to the flexible printed circuit board 126. The printed antenna 130 is disposed on the first printed circuit board 127. The second printed circuit board 128 covers the bottom surface 114 of the battery unit 110 and includes a connector 129. The physical condition sensor 140 is disposed on the second printed circuit board 128. The flexible printed circuit board 126 is bended to cover the one of the side surfaces 116 and engaged with the connector 129 for electrically connecting the first printed circuit board 127 and the second printed circuit board 128.

Figure 8:
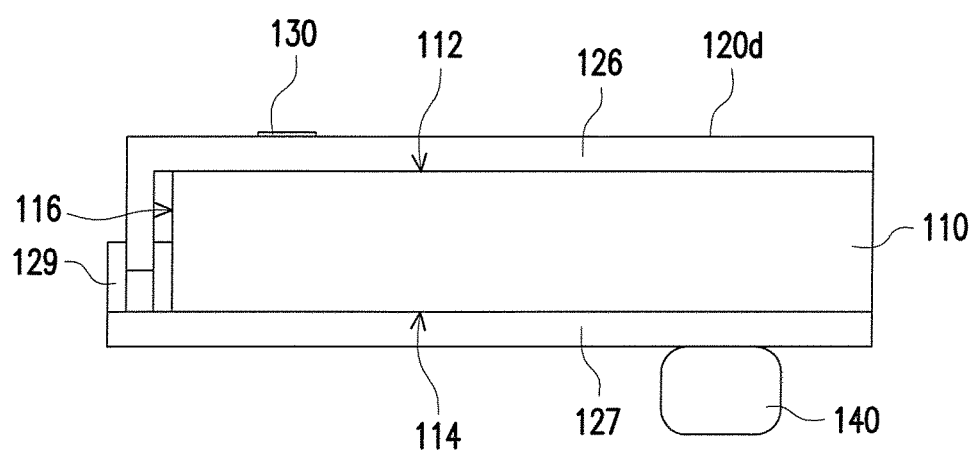
FIG. 8 illustrates a partial cross-sectional view of an attachable monitoring device according to another embodiment of the invention.

FIG. 8 illustrates a partial cross-sectional view of an attachable monitoring device according to another embodiment of the invention. It is noted that the attachable monitoring device 100d shown in FIG. 8 contains many features same as or similar to the attachable monitoring device 100 disclosed earlier with FIG. 1. For purpose of clarity and simplicity, detail description of same or similar features may be omitted; also, the attachable monitoring device 100d shown in FIG. 8 merely illustrate the core portion (the wiring board unit and the battery unit) thereof, and detail illustration of same or similar features are omitted herein.

The main differences between the attachable monitoring device 100d and the attachable monitoring device 100 are that the wiring board unit 120d includes a flexible printed circuit board 126 and a printed circuit board 127. The flexible printed circuit board 126 is bended to cover the top surface 112 and the one of the side surfaces 116 of the battery unit 110. The printed antenna 130 is disposed on the flexible printed circuit board 126. The printed circuit board 127 covers the bottom surface 114 of the battery unit 110 and includes a connector 129. The physical condition sensor 140 is disposed on the printed circuit board 127. The flexible printed circuit board 126 is bended to cover the one of the side surfaces 116 and engaged with the connector 129 for electrically connecting the printed circuit board 127.

In sum, the attachable monitoring device of the present invention utilizes the wiring board unit covering the top surface, the bottom surface and one of the side surfaces of the battery unit and electrically connected to the battery unit 110. With the disposition, the wiring board unit can be electrically connect two opposite surfaces of the battery unit, so that the components of the attachable monitoring device can be disposed on the two opposite surfaces of the battery unit, so as to improve space utilization of the attachable monitoring device and further reduce the overall size of the attachable monitoring device.

Also, the printed antenna and the physical condition sensor of the attachable monitoring device can be disposed at two opposite surface of the wiring board unit respectively, so as to keep a certain distance between the printed antenna and the physical condition sensor to avoid interference. Therefore, the attachable monitoring device of the present invention can also improve the performance thereof without increasing the length of the attachable monitoring device. In addition, the wiring board can be a flexible printed circuit board, so it can be bended to cover the top surface, the bottom surface and the one of the side surfaces of the battery unit. Therefore, the flexible printed circuit board can provide flexibility to the attachable monitoring device, so as to provide better comfort to the user when the attachable monitoring device is in direct contact with the body of the user.

Moreover, with the printed antenna printed on the wiring board, the physical-condition signals detected by the physical condition sensor can be uploaded to the cloud via, for example, Bluetooth, Wi-Fi, third generation (3G), Long Term Evolution (LTE), or other suitable wireless communication means. In the present invention, the attachable monitoring device can associate with both internet (on line) and telecommunication (off line) networks to perform real-time early warning and/or physical condition prediction (for fertility) to inform caregivers in time.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. An attachable monitoring device for detecting a physical condition of a user, comprising:
   a battery unit comprising a top surface, a bottom surface opposite to the top surface and a plurality of side surfaces connecting the top surface and the bottom surface;
   a wiring board unit covering the top surface, the bottom surface and one of the side surfaces and electrically connected to the battery unit, the wiring board unit comprising a printed antenna printed on a first outer surface of the wiring board unit, a first printed circuit board covering the top surface, a second printed circuit board covering the bottom surface and a connector covering the one of the side surfaces and connecting the first printed circuit board and the second printed circuit board for electrically connecting the first printed circuit board and the second printed circuit board;
   a physical condition sensor disposed on a second outer surface of the wiring board unit opposite to the first outer surface, the physical condition sensor comprising a sensing region for contacting the user to detect a physical-condition signal of the user; and
   an adhesive disposed on the wiring board unit for being attached to a body of the user.

2. The attachable monitoring device according to claim 1, wherein the wiring board unit further comprising a power pad contacting the battery unit for electrically connecting the battery unit and the wiring board unit.

3. The attachable monitoring device according to claim 1, wherein the wiring board unit is a flexible printed circuit board bended to cover the top surface, the bottom surface and the one of the side surfaces.

4. The attachable monitoring device according to claim 1, wherein the printed antenna is disposed on the first printed circuit board, and the physical condition sensor is disposed on the second printed circuit board.

5. The attachable monitoring device according to claim 1, wherein the first printed circuit board further comprises a plurality of first pins, the second printed circuit board further comprises a plurality of second pins, two opposite ends of the connector are engaged with the first pins and the second pins respectively.

6. An attachable monitoring device for detecting a physical condition of a user, comprising:
   a battery unit comprising a top surface, a bottom surface opposite to the top surface and a plurality of side surfaces connecting the top surface and the bottom surface;
   a wiring board unit covering the top surface, the bottom surface and one of the side surfaces and electrically connected to the battery unit, the wiring board unit comprising a printed antenna printed on a first outer surface of the wiring board unit, wherein the wiring board unit comprises a first printed circuit board and a second printed circuit board, the first printed circuit board covers the top surface and comprises a plurality of pins, the second printed circuit board covers the bottom surface and comprises a connector corresponding to the pins, the connector covers the one of the side surfaces and engaged with the pins for electrically connecting the first printed circuit board and the second printed circuit board;
   a physical condition sensor disposed on a second outer surface of the wiring board unit opposite to the first outer surface, the physical condition sensor comprising a sensing region for contacting the user to detect a physical-condition signal of the user; and
   an adhesive disposed on the wiring board unit for being attached to a body of the user.

7. The attachable monitoring device according to claim 6, wherein the printed antenna is disposed on the first printed circuit board, and the physical condition sensor is disposed on the second printed circuit board.

8. An attachable monitoring device for detecting a physical condition of a user, comprising:
   a battery unit comprising a top surface, a bottom surface opposite to the top surface and a plurality of side surfaces connecting the top surface and the bottom surface;
   a wiring board unit covering the top surface, the bottom surface and one of the side surfaces and electrically connected to the battery unit, the wiring board unit comprising a printed antenna printed on a first outer surface of the wiring board unit, wherein the wiring board unit comprises a first printed circuit board, a flexible printed circuit board and a second printed circuit board, the first printed circuit board covers the top surface and is connected to the flexible printed circuit board, the second printed circuit board covers the bottom surface and comprises a connector, the flexible printed circuit board is bended to cover the one of the side surfaces and engaged with the connector for electrically connecting the first printed circuit board and the second printed circuit board;
   a physical condition sensor disposed on a second outer surface of the wiring board unit opposite to the first outer surface, the physical condition sensor comprising a sensing region for contacting the user to detect a physical-condition signal of the user; and
   an adhesive disposed on the wiring board unit for being attached to a body of the user.

9. The attachable monitoring device according to claim 8, wherein the printed antenna is disposed on the first printed circuit board, and the physical condition sensor is disposed on the second printed circuit board.

10. An attachable monitoring device for detecting a physical condition of a user, comprising:
    a battery unit comprising a top surface, a bottom surface opposite to the top surface and a plurality of side surfaces connecting the top surface and the bottom surface;
    a wiring board unit covering the top surface, the bottom surface and one of the side surfaces and electrically connected to the battery unit, the wiring board unit comprising a printed antenna printed on a first outer surface of the wiring board unit, wherein the wiring board unit comprises a flexible printed circuit board and a printed circuit board, the flexible printed circuit board is bended to cover the top surface and the one of the side surfaces, the printed circuit board covers the bottom surface and comprises a connector engaged with the flexible printed circuit board for electrically connecting the first printed circuit board and the second printed circuit board;
    a physical condition sensor disposed on a second outer surface of the wiring board unit opposite to the first outer surface, the physical condition sensor comprising a sensing region for contacting the user to detect a physical-condition signal of the user; and
    an adhesive disposed on the wiring board unit for being attached to a body of the user.

11. The attachable monitoring device according to claim 10, wherein the printed antenna is disposed on the flexible printed circuit board, and the physical condition sensor is disposed on the printed circuit board.

12. The attachable monitoring device according to claim 1, further comprising a wireless communication switch disposed on the first outer surface and electrically connected to the printed antenna.

13. The attachable monitoring device according to claim 1, further comprising an isolation enclosure covering the battery unit and the wiring board unit and exposing the sensing region.

14. The attachable monitoring device according to claim 13, wherein materials of the isolation enclosure comprises thermal plastic materials, and the isolation enclosure is formed by injection molding.

15. The attachable monitoring device according to claim 13, further comprising a wireless communication switch electrically connected to the printed antenna, and the isolation enclosure exposing the wireless communication switch.

16. The attachable monitoring device according to claim 13, further comprising an isolation coating filled between the isolation enclosure and the wiring board unit.

17. The attachable monitoring device according to claim 16, wherein the isolation coating further comprises an electrical insulation coating and a waterproof coating.

18. The attachable monitoring device according to claim 1, wherein the adhesive is disposed on the second outer surface and exposes the sensing region.

* * * * *